United States Patent

Soon–Shiong et al.

[11] Patent Number: 5,545,423
[45] Date of Patent: Aug. 13, 1996

[54] CYTOPROTECTIVE, BIOCOMPATIBLE, RETRIEVABLE MACROCAPSULE CONTAINMENT SYSTEMS FOR BIOLOGICALLY ACTIVE MATERIALS

[75] Inventors: Patrick Soon–Shiong; Neil P. Desai; Roswitha E. Heintz, all of Los Angeles, Calif.

[73] Assignee: VivoRx, Inc., Santa Monica, Calif.

[21] Appl. No.: 400,442

[22] Filed: Mar. 6, 1995

Related U.S. Application Data

[63] Continuation of Ser. No. 981,852, Nov. 24, 1992, abandoned, which is a continuation-in-part of Ser. No. 797,704, Nov. 25, 1991, abandoned.

[51] Int. Cl.$^6$ .............................. A61K 9/48; A61K 9/50; C12N 11/00
[52] U.S. Cl. ..................... 424/484; 424/486; 424/489; 424/490; 424/491; 424/499; 435/174; 435/177; 435/180; 435/182; 514/866
[58] Field of Search ........................... 424/484, 486, 424/489, 490, 491, 499; 435/174, 177, 180, 182; 514/866

[56] References Cited

U.S. PATENT DOCUMENTS

| | | | |
|---|---|---|---|
| 4,352,883 | 10/1982 | Lim | 435/178 |
| 4,663,286 | 5/1987 | Tsang et al. | 435/178 |
| 4,833,081 | 5/1989 | Walker | 435/182 |
| 5,084,350 | 1/1992 | Chang et al. | 428/402.2 |

FOREIGN PATENT DOCUMENTS

030177A1  2/1989  European Pat. Off.

*Primary Examiner*—Gollamudi S. Kishore
*Attorney, Agent, or Firm*—Pretty, Schroeder, Brueggemann & Clark; Stephen E. Reiter

[57] ABSTRACT

The present invention is directed to a macrocapsule for encapsulating microcapsules containing biologically active material, such as living cells or free living cells, to make the system more biocompatible by decreasing the surface area and surface roughness of microencapsulated biological materials; increasing mechanical stability of microencapsulated biological materials; enhancing cytoprotectivity by increasing diffusion distance of encapsulated biological material from cytotoxins secreted in vivo; providing retrievability of microencapsulated material; and providing a system of sustained release of the cellular products. The method for producing such a macrocapsule containing the microcapsules is also disclosed.

10 Claims, 5 Drawing Sheets

CYTOPROTECTIVE, BIOCOMPATIBLE, RETRIEVABLE MACROCAPSULE CONTAINMENT SYSTEMS FOR BIOLOGICALLY ACTIVE MATERIALS

This application is a continuation of application Ser. No. 07/981,852, filed Nov. 24, 1992, now abandoned, which is a continuation-in-part of U.S. application Ser. No. 07/797,704, filed Nov. 25, 1991, now abandoned.

The present invention relates to a new form of biocompatible materials which envelop encapsulated or free cells to provide an immune barrier. The resulting encapsulated material is generally small, but macroscopic, so that it is retrievable in situ. More specifically the present invention relates to a composition and system for treatment of diabetes.

BACKGROUND OF THE INVENTION

Diabetes Mellitus is a serious disease afflicting over 100 million people worldwide. In the United States, there are more than 12 million diabetics, with 600,000 new cases diagnosed each year. Insulin-dependent, or Type I diabetics, require daily injections of insulin to prevent them from lapsing into coma.

With the discovery of insulin in 1928, it was thought that diabetes had been cured. Unfortunately, despite insulin therapy, the major complications of the disease caused by high blood sugar levels persist. Each year, diabetes accounts for 40,000 limb amputations and 5,000 new cases of blindness in the United States. Among teenagers, diabetes is the leading cause of kidney failure. Data from the National Institutes of Health show that the rate of heart disease and stroke is twice as great in diabetics than in the general population.

The diabetic patient faces a 30% reduced lifespan. Multiple insulin injections given periodically throughout the day cannot duplicate the precise feedback of insulin secretion from the pancreas. The only current method of achieving minute-to-minute glucose control is by pancreas transplantation.

While whole organ pancreas transplantation represents a significant advance in diabetes therapy, the operation is technically difficult, of limited success and use because of the problems of rejection, and it still presents a significant risk to the patient. An attractive alternative would be to extract the insulin-producing cells (islets) from a donor pancreas and to inject these cells into the diabetic patient, thus effecting a cure. The use of such cells, however, would still run the risk of rejection by the host.

Microencapsulation of islets by an alginate-PLL-alginate membrane (i.e., an alginate-poly-L-lysine-alginate membrane) is a potential method for prevention of rejection by the host's immune system. By this technique, researchers are able to encapsulate living islets in a protective membrane that allows insulin to be secreted, yet prevents antibodies from reaching the islets, causing rejection of the cells. This membrane (or microcapsule) protects the islet from rejection and allows insulin to be secreted through its "pores" to maintain the diabetic in normal glucose control.

Successful transplants of microencapsulated islets have not been clinically feasible to date due to fundamental problems of transplant rejection and/or a fibrotic reaction to the microcapsule membrane. Lim and Sun, 1980, reported the first successful implantation of microencapsulated islets and described normalization of blood sugar in diabetic rats. However, for microencapsulated islets to be clinically useful and applicable in humans, it is important that the immunoprotective membrane be biocompatible, allow adequate diffusion for the encapsulated cells to respond appropriately to a stimulatory signal, provide the encapsulated cells with necessary nutrients, and be retrievable. Retrievability is desirable for a variety of reasons, e.g., so that accumulation of the implanted materials can be avoided, so that encapsulated cells can be removed from the recipient when no longer needed or desired (e.g., when the product(s) of the encapsulated cells are no longer needed, if the encapsulated cells fail to perform as desired, etc.), so that encapsulated cells can be removed if/when they become non-viable, and the like. Currently there are no reports of successful reversal of diabetes in humans by transplantation of encapsulated islets.

Biocompatibility of encapsulated islets remains a fundamental problem. The term "biocompatible" is used herein in its broad sense, and relates to the ability of the material to result in long-term in vivo function of transplanted biological material, as well as its ability to avoid a foreign body, fibrotic response. A major problem with microencapsulation technology has been the occurrence of fibrous overgrowth of the epicapsular surface, resulting in cell death and early graft failure. Despite extensive studies, the pathological basis of this phenomenon in alginate based capsules remains poorly understood. However, several factors have recently been identified as being involved in graft failure, e.g., the guluronic acid/mannuronic acid content of the alginate employed, imperfections in the microcapsule membrane (allowing exposure of poly-L-lysine to the in vivo environment), failure of the microcapsule membrane to completely cover the cells being encapsulated (thereby allowing exposure of the cells to the in vivo environment), and the like.

Alginate is a polysaccharide isolated from marine brown algae including *Laminaria hyperborea, Laminaria digitata, Ascophyllum nodosum* and *Macrocystis pyrifera*. Alginate forms ionically crosslinked gels with most di- and multivalent cations. Calcium cations are most widely used, and give rise to a three-dimensional network in the form of an ionically crosslinked gel by inter-chain binding between G-blocks. (Skjåk-Bræk, 1988).

It has recently been demonstrated that the mannuronic acid residues are the active cytokine inducers in alginate, and since these cytokines (IL-1 and TNF) are known to be potent stimulators of fibroblast proliferation (Otterlei et al., 1991), it was deduced that alginate capsules high in mannuronic acid content (M-content) were responsible in part for the fibrotic response reported in the past (Soon-Shiong et al. 1991). More significantly, it has been found that this reaction could be ameliorated by increasing the guluronic acid content (G-content) of the alginate capsule since guluronic acid appears not to be immunostimulating. Furthermore, it has been demonstrated that cyclosporin A resulted in a dose dependent inhibition of mannuronic acid-induced TNF and IL-1 stimulation of human monocytes in vitro. Based on this information, it has been hypothesized that the fibrotic reaction of the microcapsule could be ameliorated in part by an alginate formulation high in guluronic acid content, as well as a subtherapeutic course of cyclosporin A to inhibit cytokine stimulation. By this method, diabetes in the spontaneous diabetic dog model has been successfully reversed by transplantation of donor islets encapsulated in high G-content alginate (Soon-Shiong et al. 1991).

Polyethylene glycols (PEG; also referred to as polyethylene oxide, PEO) have been investigated extensively in recent years for use as biocompatible, protein repulsive, noninflammatory, and nonimmunogenic modifiers for drugs, proteins, enzymes, and surfaces of implanted materials. The basis for these extraordinary characteristics has been attributed to the flexibility of the polymer backbone, and the volume exclusion effect of this polymer in solution or when immobilized at a surface. The solubility of PEGs in water, as well as a number of common organic solvents, facilitates modification by a variety of chemical reactions. A recent review (Harris, 1985) describes the synthesis of numerous derivatives of PEG and the immobilization thereof to surfaces, proteins, and drugs.

PEG bound to bovine serum albumin has shown reduced immunogenicity and increased circulation times in a rabbit (Abuchowski et al., 1977). Drugs such as penicillin, aspirin, amphetamine, quinidine, procaine, and atropine have been attached to PEG in order to increase their duration of activity as a result of slow release (Weiner et al., 1974; Zalipsky et al., 1983). PEG covalently bound to poly-L-lysine (PLL) has been used to enhance the biocompatibility of alginate-PLL microcapsules used for the encapsulation of cells. PEG has been covalently bound to polysaccharides such as dextran (Pitha et al., 1979, Duval et al., 1991), chitosan (Harris et al., 1984) and alginates (Desai et al., 1991). These modifications confer organic solubility to the polysaccharides.

Surfaces modified with PEG were found to be extremely nonthrombogenic (Desai and Hubbell, 1991a; Nagoaka and Nakao, 1990), resistant to fibrous overgrowth in vivo (Desai and Hubbell, 1992a) and resistant to bacterial adhesion (Desai and Hubbell, 1992b). Solutions containing PEG have also been found to enhance the preservation of organs for transplantation (Collins et al.; Zheng et al., 1991). The basis of the preservation activity is not clearly understood but has been attributed to adhesion of PEG to cell surface molecules with a resultant change in the presentation of antigen so as to alter the nature of the immune response.

Crosslinked PEG gels have been prepared and utilized for immobilization of enzymes and microbial cells. Fukui and Tanaka (1976) and Fukui et al., (1987) have prepared polymerizable derivatives of PEG (such as the dimethacrylate) and photocrosslinked them with UV light in the presence of a suitable initiator to form a covalently crosslinked gel. Kumakura and Kaetsu (1983) have reported the polymerization and crosslinking of diacrylate derivatives of PEG by gamma radiation for the purpose of immobilizing microbial cells. Due to the mild nature of the photopolymerization, i.e., absence of heating, without shifting pH to extreme values, and without the use of toxic chemicals, the Fukui and Tanaka (1976) publication suggests that this technique is desirable for the entrapment not only of enzymes, but also for cells and organelles.

Dupuy et al. (1988) have recently described a photopolymerization process for the entrapment of agarose embedded pancreatic islets in microspheres of crosslinked acrylamide. However, this reference describes entrapment of individual microspheres, but does not describe further entrapment of these already entrapped cells. Visible light was used as the initiating radiation in the presence of a photochemical sensitizer (vitamin B2, i.e., riboflavin), and a cocatalyst (N-N-N'N'-tetramethylethylene diamine). A high pressure mercury lamp was used as the source of visible radiation and the islets were demonstrated to maintain a good viability in vitro following the polymerization step.

Visible radiation between wavelengths of 400–700 nm have been determined to be nontoxic to living cells (Karu, 1990; Dupuy et al., 1988). A recent review (Eaton, 1986) describes a variety of dyes and cocatalysts that may be used as polymerization initiators in the presence of appropriate visible radiation.

In recent years considerable interest has been expressed in the use of lasers for polymerization processes (Wu, 1990). These polymerizations are extremely fast and may be completed in milliseconds (Decker and Moussa, 1989; Hoyle et al., 1989; Eaton, 1986). The use of coherent radiation often results in the polymerization being innocuous to living cells. This arises from the use of wavelength specific chromophores as the polymerization initiators, and these chromophores are typically the only species in the polymer/cell suspension that absorb the incident radiation.

SUMMARY OF THE INVENTION

It has previously been demonstrated that Type I insulin-dependent diabetes can be reversed in rats and dogs by implantation of micro-encapsulated pancreatic islets in the peritoneal cavity of these animals using both allograft (dog islets to dog recipients) and xenograft (dog islets to rat recipients) models (Soon-Shiong et al., 1991). The alginate microcapsules employed in these studies provide immuno-protectivity, and result in graft survival of allografts for several months in the absence of immunosuppression. The alginate gels, however, are ionically crosslinked and, therefore, are subject to breakage and resorption as a result of ionic equilibration in vivo. In addition, free microcapsules are difficult to retrieve due to their small size (200–600 µm) and nonlocalization within the peritoneal cavity.

While it is known that the mannuronic acid—guluronic acid (M—G) ratio of the alginate employed plays an important role in preventing fibrosis, in accordance with the present invention, other factors involving various defects in prior art microcapsules have been identified which play an important role in preventing long term viability of the transplanted graft. Photomicrographs demonstrate these heretofore unrecognized defects in prior art microcapsules.

In accordance with the present invention, a number of factors relating to capsule failure, i.e., likelihood of inducing an immune response, likelihood of loss of function due to death of the encapsulated cells, the degree of protection afforded encapsulated cells, and the like, have been identified, i.e., that:

(i) Both mechanical and chemical stability of the microcapsule play a critical role in fibrous overgrowth. It has been discovered that the water-soluble membrane dissolves over a prolonged period of in vivo exposure, eventually exposing the encapsulated material to the host's immune system, initiating a rejection response;

(ii) The "roughness" of the capsule membrane, as well as defective microcapsules, result in macrophage activation, cell adherence, cellular overgrowth and eventual fibrosis;

(iii) Disruption or breakage of microcapsules, with cracks in the capsule membrane, results in fibrosis;

(iv) While alginate, specifically high G-content alginate, is relatively biocompatible, it has been discovered that poly-L-lysine (PLL) is a potent stimulator for fibrous overgrowth in vivo. Indeed, the prior art describes attempts to cover the outer coat of PLL with an outer layer of alginate to prevent this overgrowth problem. However, according to the present invention, it has been discovered that any disruption of the membrane, or any imperfection of coating of the membrane results in fibrous overgrowth when polymer materials such as PLL are exposed. Furthermore, current methods of covering PLL with an outer layer of alginate are ineffective to fully prevent some exposure of PLL over time, in vivo; and (v) Exposure of biologically active material on the surface of the microcapsule (because such material is not adequately entrapped in the gel forming the microcapsule) exposes such material to the host's immune system, initiating an immune response.

In accordance with the present invention, it has been further discovered that individual spherical microcapsules provide a large exposed surface area, facilitating transport of nutrients through the membrane, while on the other hand, increasing the probability of cell adherence and fibrous overgrowth. It has been found that by reducing this exposed microcapsule surface area and/or by reducing exposure of any unbound, positively charged polylysine, while maintaining the critical diffusion capacity of the immuno-protective membrane, increased biocompatibility will ensue. By reduction of exposed microcapsule surface area, the percentage of "roughness" associated with each individual microcapsule would be reduced, resulting in improved biocompatibility. In addition, in accordance with the present invention, it has been recognized that improving mechanical integrity of the capsule is an important step in achieving long term graft function.

In accordance with the present invention, it has been found that long term graft function can be achieved by entrapping or encasing biologically active material, optionally contained within a microcapsule (e.g., individual microencapsulated cells) in a macrocapsule which is biocompatible, thereby (i) increasing the cytoprotectivity of the entrapped individually encapsulated cells, (ii) reducing exposure of unbound positively charged polylysine to the host in vivo environment, (iii) enhancing the mechanical stability of the capsular membrane, (iv) reducing the exposed microcapsule surface area roughness; and (v) reducing the exposure of cells adhering to the surface of the microcapsule to the host in vivo environment; all of the above advantages are obtained while (vi) maintaining the diffusion capacity of the polymeric material used for encapsulation, thereby allowing the entrapped encapsulated cells to be nourished and respond to a stimulatory signal.

Additionally, macrocapsules of the present invention provide a system of rapid but sustained release of the material made by and secreted by the encapsulated cell(s), which in turn provides for more regulated control of physiological processes (e.g., blood glucose levels in the case of encapsulated islets). Specifically, in response to an intravenous glucose stimulus, insulin release occurs more rapidly from encapsulated islets entrapped within a macrocapsule than from free floating microencapsulated islets, as demonstrated by the in vivo intravenous glucose stimulation studies described in Example 9, below. In addition, insulin release from these gel entrapped microcapsules is sustained over a longer period of time, as demonstrated by the in vitro glucose stimulation studies described in Example 8, below.

The present invention also permits retrievability of the implant because of its macroscopic size and its grouping of the various microencapsulated islets into a single package or a plurality of macroscopic packages. Retrievability is desirable for a variety of reasons, e.g., so that accumulation of the implanted materials can be avoided, so that encapsulated cells can be removed from the recipient when no longer needed or desired (e.g., when the product(s) of the encapsulated cells are no longer needed, if the encapsulated cells fail to perform as desired, etc.), so that encapsulated cells can be removed if/when they become non-viable, and the like.

The present invention overcomes the problems of the prior art by improving the cytoprotectivity and biocompatibility of implanted biological systems. The present invention also provides a gel entrapment system which provides a rapid response of entrapped cells to a stimulatory signal. The present invention further provides a sustained release system made from microencapsulated cells which are further packaged in a macrocapsule. The present invention also provides a system that localizes microcapsules in a particular region (e.g., a region of high vascularization such as the omentum), as well as a system which minimizes the breakage of microcapsules, and facilitates their ready retrieval.

As will be readily apparent to a person of skill in the art, the macrocapsules of the present invention may be used to entrap not only encapsulated or unencapsulated living cells, but also any chemical reagents which may have a pharmacological or physiological effect upon sustained release by the system disclosed herein.

DETAILED DESCRIPTION OF THE INVENTION

Figure 1:
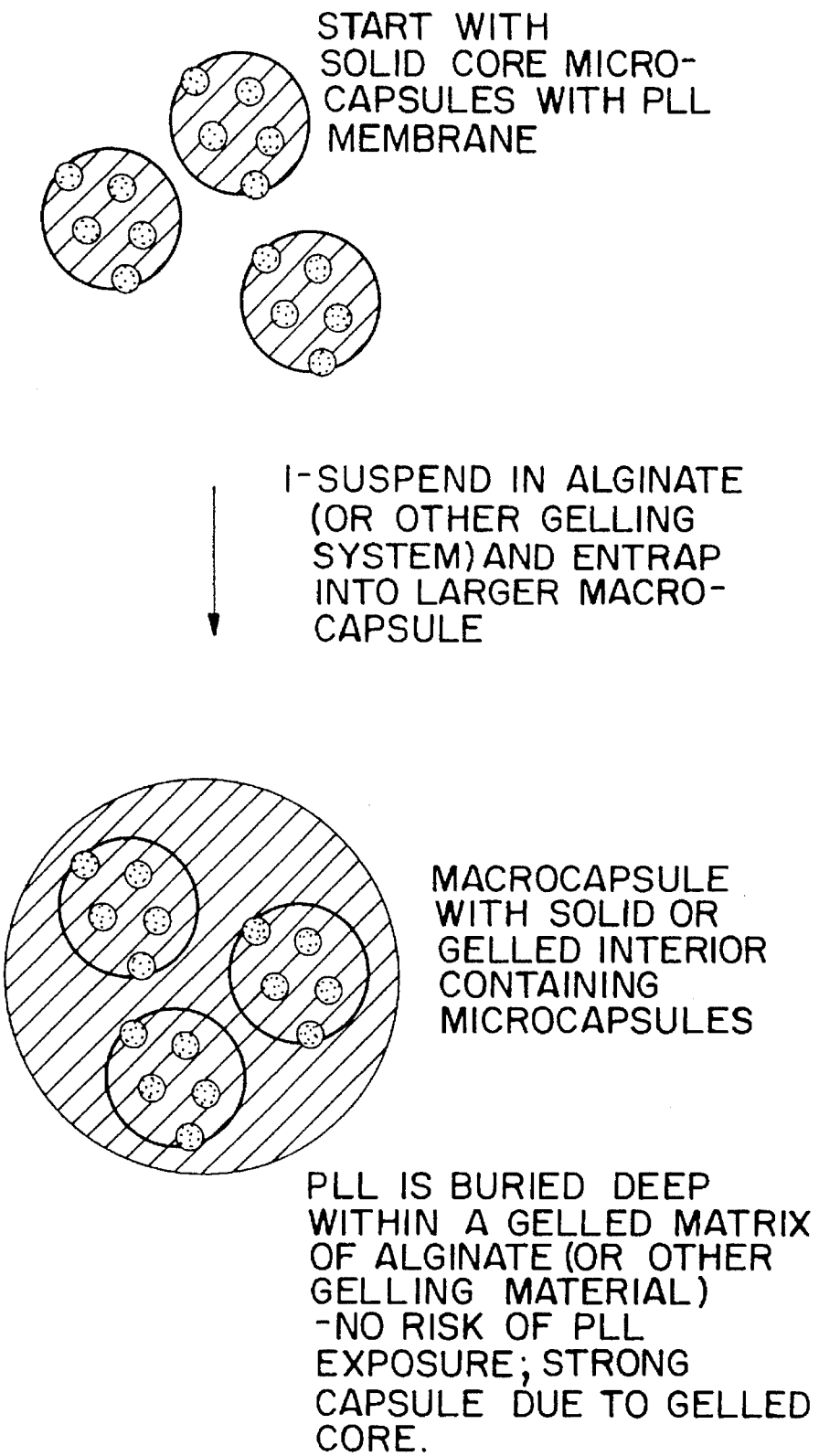
FIG. 1 is a drawing of one embodiment of a macrocapsule of the present invention containing encapsulated biological material.

The following specification describes materials and methods of macroencapsulating biologically active materials, such as living cells, to provide an enhanced biocompatible, retrievable system which is useful, for example, for cell containment and transplantation. In the following description, numerous details such as specific materials and methods are set forth in order to provide a more complete understanding of the present invention. It is understood by those skilled in the art that the present invention can be practiced without these specific details. In other instances, well known materials and methods are not described in detail so as not to obscure the present invention. In addition, the following description is given with particular reference in many instances to islets and diabetes treatment. This description is given as a presently preferred application of the present invention. Nonetheless, it is apparent that the present invention is not limited to the treatment of a single disease state. The present invention can be used equally as well for other cell types and treatment of other disorders or for other physiological purposes and could be used with microencapsulated cells or unencapsulated cells of any type.

As part of the work carried out pursuant to the present invention, photomicrographs were taken of prior art alginate-PLL-alginate microcapsules in efforts to identify the faults and defects therein [see, for example, Clayton, in J. Microencapsulation 8:221–233 (1991) and Wijsman et al., in J. Transplantation 54:588–592 (1992) for a description of prior art microcapsules]. The resulting micrographs readily reveal the faults and defects in prior art microcapsules. For example, a photomicrograph (40x) of an empty alginate-PLL-alginate microcapsule (retrieved from the peritoneal cavity of a rat) demonstrates that cellular overgrowth (appearing as a darkened area) occurs in areas of the exposed microcapsule gel or in areas of exposed polylysine when capsular membrane integrity is lost. A photomicrograph (100x) of an alginate-PLL-alginate encapsulated islet shows areas of "roughness" or "stress marks" associated with individual microcapsules. The surface area of such individual microcapsules is large and thus in turn, the exposure of "rough" surfaces is huge, increasing the risk of cellular overgrowth. In addition, imperfect covering of polylysine by an outer coat of alginate results in potential overgrowth.

A photomicrograph (40x) of a defective empty microcapsule, amongst intact empty alginate microcapsules, all retrieved at the same time from the peritoneal cavity of a rat, demonstrates cellular overgrowth (which appears as darkened areas). Vigorous overgrowth is observed to be associated only with the defective capsule. This provides further evidence that minor imperfections invoke a foreign body response to defective capsules and to exposed capsular material, especially PLL.

A photomicrograph (40x) of disrupted alginate microcapsules containing canine islets (transplanted free floating into the peritoneal cavity), retrieved from the peritoneal cavity of a diabetic dog when reversal of diabetes failed, shows the presence of disrupted capsules, providing evidence that loss of mechanical stability plays an important role in graft failure. These microencapsulated canine islets successfully reversed diabetes, but only for a short period.

As used herein, the term "macrocapsule" means a capsule of gel material surrounding biologically active material, optionally contained within a microcapsule (e.g., one or more microcapsules, where each microcapsule contains at least one living cell, such as islets or other pharmacological agent producing cells, or certain drugs or physiologically active agents). The term "macrocapsule" may include "macro-membranes," "macrogels," "gel entrapped microcapsules," "lace," "noodles," "teabags," "threads," "worms," and the like, which a person of skill in the art would understand refers to the general class of compositions described herein. While the actual dimensions of the various components of the invention particles are not critical, the term "microcapsules" is generally used to refer to particles wherein the largest dimensions thereof fall in the range of about 5 up to 4000 microns, while the term "macrocapsules" is generally used to refer to particles wherein the largest dimensions thereof fall in the range of about 500 microns up to about 50 cm. What is important according to the present invention is that the contents of a microcapsule be further encapsulated into a macrocapsule, thereby affording the added benefits of the macroencapsulating polymer, as described herein.

In accordance with the present invention, biologically active material, e.g., a plurality of cell-containing microcapsules, are covered with a thick layer of gelled material, forming a microcapsule-containing macrocapsule. A schematic showing a cross-section of such a macrocapsule is provided in FIG. 1. Inspection of the Figure reveals that the macrocapsule itself contains no polycation or other fibrogenic surface; instead, the immunoprotective membrane (i.e., polycation such as PLL) is localized at the surface of the microcapsules, which are buried deep within the macrocapsule (and protected from exposure to the in vivo environment by thousands of molecular layers). The core of the microcapsules (as well as the macrocapsule itself) are maintained in the gelled state (i.e., crosslinked or insoluble form), in contrast to prior art encapsulation systems, wherein the core material is liquified.

Generally the layer of gelled material in invention macrocapsules has a thickness of at least about 1 micron, with a thickness of at least about 20–40 microns being preferred, and a thickness of at least about 50 microns or greater being especially preferred. This provides more effective masking of the polycation layer on the microcapsule than the few molecule thickness (of alginate outer layer) achieved in the preparation of prior art microcapsules. The layer of gelled material in invention macrocapsules prevents direct exposure of any immunogenic agents at the microcapsule surface (e.g., polycations, unencapsulated cells, and the like) to the in vivo environment, thereby preventing immune response triggered by prior art microcapsules. In addition, the layer of gelled material is exceptionally stable to long-term exposure to physiological conditions since the gelled material is ionically and/or covalently crosslinked to itself, and does not depend on an interaction with the incorporated material for strength and/or stability. This is in direct contrast with alginate outer layers employed in prior art microcapsules, wherein the sole means of anchorage of the alginate outer layer to the capsule is the the formation of a charge complex (i.e., ionic interaction) between the alginate and the polycation immunoprotective layer.

In a preferred embodiment of the present invention, when microcapsules are incorporated into macrocapsules, the microcapsules (and the macrocapsules themselves) are maintained in the gelled state (i.e., ionically and/or covalently crosslinked). This is contrary to the teachings of the prior art, wherein the encapsulating matrix of the microcapsule is liquified prior to implantation. In accordance with the present invention, it has surprisingly been found that the diffusion of nutrients in, and products of the encapsulated cells out of invention macrocapsules is highly efficient.

Macrocapsules of the invention can be produced in a variety of shapes, i.e., in the shape of a cylinder (i.e., a geometrical solid generated by the revolution of a rectangle about one of its sides), a sphere (i.e., a solid geometrical figure generated by the revolution of a semicircle around its diameter), a disc (i.e., a generally flat, circular form), a flat sheet (i.e., a generally flat polygonal form, preferably square or rectangular), a wafer (i.e., an irregular flat sheet), a dog-bone (i.e., a shape that has a central stem and two ends which are larger in diameter than the central stem, such as a dumbell), or the like.

The materials used to provide such entrapment could be alginate (preferably high G-content alginate), or a modification of such alginate to improve its biocompatibility and stability, e.g., a polymerizable alginate allowing covalent crosslinkage, or crosslinkable or polymerizable, water soluble polyalkylene glycol, or combinations of these materials. The process to cause gel entrapment of such materials can be accomplished either by ionic or covalent crosslinkage.

Macrocapsules contemplated for use in the practice of the present invention contain therein biologically active material, wherein said biologically active material is optionally contained within microcapsules (i.e., a plurality of microcapsules within said macrocapsule). The invention macrocapsule can be prepared from a variety of polymeric materials, such as, for example, covalently crosslinkable or polymerizable linear or branched chain PEG, mixtures of different molecular weight covalently crosslinkable or polymerizable linear or branched chain PEGs, ionically crosslinkable alginate, combinations of alginate and covalently crosslinkable or polymerizable PEG and modified alginate that is capable of being covalently and ionically crosslinked, and the like.

Macrocapsules prepared in accordance with the present invention comprise biologically active material encapsulated in the above-described biocompatible crosslinkable material, wherein the macrocapsule has a volume in which the largest physical dimension is greater than 1 mm. Macrocapsules can contain "free" (i.e., unmodified by any coating) cells or groups of cells therein. Alternatively, macrocapsules may contain cells or groups of cells which are themselves encapsulated within microcapsules.

Biologically active materials contemplated for encapsulation (to produce microcapsules and/or macrocapsules) according to the present invention include individual living cells or groups of living cells, biological materials (for diagnostic purposes, e.g., for in vivo evaluation of the effects of such biological materials on an organism, and conversely, the effects of the organism on the materials), tumor cells (for evaluation of chemotherapeutic agents), human T-lymphoblastoid cells sensitive to the cytopathic effects of HIV; pharmacologically active drugs; diagnostic agents, and the like. As employed herein, the term "living cells" refers to any viable cellular material, regardless of the source thereof. Thus, virus cells, prokaryotic cells, and eukaryotic cells are contemplated. Specifically contemplated cells include islets of Langerhans (for the treatment of diabetes), dopamine secreting cells (for the treatment of Parkinsons disease), nerve growth factor secreting cells (for the treatment of Alzheimer's disease), hepatocytes (for treatment of liver dysfunction), adrenaline/angiotensin secreting cells (for regulation of hypo/hypertension), parathyroid cells (for replacing thyroid function), norepinephrine/metencephalin secreting cells (for the control of pain), hemoglobin (to create artificial blood), and the like.

Covalently crosslinkable and/or polymerizable polyethylene glycols (PEGs) contemplated for use in the practice of the present invention include linear or branched chain PEGs (including STAR PEGs) modified with a substituent X which is capable of undergoing free radical polymerization (X is a moiety containing a carbon-carbon double bond or triple bond capable of free radical polymerization; and X is linked covalently to said PEG through linkages selected from ester, ether, thioether, disulfide, amide, imide, secondary amines, tertiary amines, direct carbon-carbon (C—C) linkages, sulfate esters, sulfonate esters, phosphate esters, urethanes, carbonates, and the like). Examples of such covalently crosslinable polyethylene glycols include vinyl and allyl ethers of polyethylene glycol, acrylate and methacrylate esters of polyethylene glycol, and the like.

PEGs having a wide range of molecular weights can be employed in the practice of the present invention, thus mixtures of different molecular weights of covalently crosslinkable PEGs contemplated for use in the practice of the present invention include PEGs having a MW in the range of about 200 up to 1,000,000 (with molecular weights in the range of about 500 up to 100,000 preferred, and PEGs having molecular weights in the range of about 1000 to 50,000 being the presently most preferred). Such PEGs can be linear or branched chain (including STAR PEGs). STAR PEGs are molecules having a central core (such as divinyl benzene) which is anionically polymerizable under controlled conditions to form living nuclei having a predetermined number of active sites. Ethylene oxide is added to the living nuclei and polymerized to produce a known number of PEG "arms", which are quenched with water when the desired molecular weight is achieved. Alternatively, the central core can be an ethoxylated oligomeric glycerol that is used to initiate polymerization of ethylene oxide to produce a STAR PEG of desired molecular weight.

Alginates contemplated for use in the practice of the present invention include high G-content alginate, high M-content alginate, sodium alginate, and the like; covalently crosslinkable alginates contemplated for use in the practice of the present invention include alginates modified with a substituent X which is capable of undergoing free radical polymerization (X is a moiety containing a carbon-carbon double bond or triple bond capable of free radical polymerization; and X is linked covalently to said alginate through linkages selected from ester, ether, thioether, disulfide, amide, imide, secondary amines, tertiary amines, direct carbon-carbon (C—C) linkages, sulfate esters, sulfonate esters, phosphate esters, urethanes, carbonates, and the like). Examples of covalently crosslinkable alginates include allyl and vinyl ethers of alginate, acrylate and methacrylate esters of alginate, and the like.

Combinations of alginate (ionically and/or covalently crosslinkable) and covalently crosslinkable PEG contemplated for use in the practice of the present invention include combinations of any two or more of the above-described alginates and PEGs.

A small amount of a comonomer can optionally be added to the crosslinking reaction to increase the polymerization rates. Examples of suitable comonomers include vinyl pyrrolidinone, acrylamide, methacrylamide, acrylic acid, methacrylic acid, sodium acrylate, sodium methacrylate, hydroxyethyl acrylate, hydroxyethyl methacrylate (HEMA), ethylene glycol diacrylate, ethylene glycol dimethacrylate, pentaerythritol triacrylate, pentaerythritol trimethacrylate, trimethylol propane triacrylate, trimethylol propane trimethacrylate, tripropylene glycol diacrylate, tripropylene glycol dimethacrylate, glyceryl acrylate, glyceryl methacrylate, and the like.

Free radical polymerization of the above-described modified materials can be carried out in a variety of ways, for example, initiated by irradiation with suitable wavelength electromagnetic radiation (e.g., visible or ultraviolet radiation) in the presence of a suitable photoinitiator, and optionally, cocatalyst and/or comonomer. Alternatively, free radical polymerization can be initiated by thermal initiation by a suitable free radical catalyst.

A variety of free radical initiators, as can readily be identified by .those of skill in the art, can be employed in the practice of the present invention. Thus, photoinitiators, thermal initiators, and the like, can be employed. For example, suitable UV initiators include 2,2-dimethoxy-2-phenyl acetophenone and its water soluble derivatives, benzophenone and its water soluble derivatives, benzil and its water soluble derivatives, thioxanthone and its water soluble derivatives, and the like. For visible light polymerization, a system of dye (also known as initiator or photosensitizer) and cocatalyst (also known as cosynergist, activator, initiating intermediate, quenching partner, or free radical generator) are used. Examples of suitable dyes are ethyl eosin, eosin, erythrosin, riboflavin, fluorscein, rose bengal, methylene blue, thionine, and the like; examples of suitable cocatalysts are triethanolamine, arginine, methyldiethanol amine, triethylamine, and the like.

Microcapsules contemplated for use in the practice of the present invention can be formed of a variety of biocompatible gel materials, such as, for example, alginate, covalently crosslinkable alginate (i.e., modified alginate that is covalently and ionically crosslinkable), covalently crosslinkable PEG, combinations of any of the above-described alginates and any of the above-described PEGs, as well as the optional presence of one or more comonomers, as described above.

Microcapsules employed in the practice of the present invention are optionally treated with an immunoprotective coating, as described by Lim in U.S. Pat. No. 4,352,883, incorporated by reference herein (Lim refers to this immunoprotective coating as a "permanent semi-permeable membrane"). Immunoprotective materials contemplated for use in the practice of the present invention include polycations (such as polyamino acids [e.g., polyhistidine, polylysine, polyornithine, and the like]; polymers containing primary amine groups, secondary amine groups, tertiary amine groups or pyridinyl nitrogen(s), such as polyethyleneimine, polyallylamine, polyetheramine, polyvinylpyridine, and the like. Treatment with such immunoprotecting materials can be carried out in a variety of ways, e.g., by crosslinking surface layers of an alginate gelled core containing encapsulated cells with polymers having acid-reactive groups such as amine or imine groups. This is typically done in a dilute solution of the selected immunoprotecting polymer. Within limits, semipermeability of the immunoprotecting coating can be controlled by proper selection of the molecular weight of the immunoprotecting polymer, its concentration, and the degree of crosslinking with the underlying gel. Molecular weight of the immunoprotecting polymer can also vary, depending on the degree of permeability desired. Typically molecular weights will fall between about 1,000 and 100,000 or higher. Presently preferred immunoprotecting polymers employed in the practice of the present invention fall in the range of about 10,000 up to 50,000. Optional treatment with immunoprotective coating can be avoided especially when the macrocapsular or microcapsular material is covalently crosslinkable, so that the desired porosity (or immunoprotectivity) may be achieved through judicious selection of the polymerizable macromonomers employed (i.e., polymerizable alginate, polymerizable PEG, and the like), as well as mixtures of such monomers.

In a presently preferred embodiment of the present invention, multiple alginate-PLL-alginate microcapsules are entrapped in an alginate macrocapsule. The microcapsules employed preferably have solid gel cores. The alginate employed can be ionically and/or covalently crosslinkable. With modified, covalently crosslinkable alginate, the introduction of polycations to control microcapsule porosity and/or to provide an immunoprotecting barrier is optional because the desired porosity (or immunoprotectivity) may be achieved by using suitable concentrations of modified alginate or by using modified alginate having different degrees of substitution with the moiety X, or combinations of such modified alginate.

Another presently preferred embodiment of the invention involves the photopolymerization of an aqueous physiological covalently crosslinkable linear or branched chain PEG (e.g., a PEG-diacrylate solution, or polymerizable equivalent) containing suspended alginate microcapsules (e.g., alginate-PLL-alginate). The microcapsules employed preferably have solid gel cores. The appropriate free radical initiators and cocatalysts are used with visible light sources such as a laser or a mercury lamp. A solid (i.e., non-liquified) gel of PEG is formed around the alginate microcapsules which in addition to providing mechanical support and retrievability, forms a nonfibrosing, cell nonadherent, and immunoprotective coating around the microcapsules. In this embodiment, the polycation layer is optional because the PEG macrocapsule can readily provide immunoprotectivity by selection of appropriate molecular weights and concentrations of crosslinkable PEGs.

In yet another presently preferred embodiment, multiple alginate-PLL-alginate microcapsules are entrapped in a macrocapsule comprising ionically and/or covalently crosslinkable alginate, and covalently crosslinkable PEG. In this embodiment as well, the polycation layer is optional because the PEG macrocapsule can readily provide immunoprotectivity by selection of appropriate molecular weights and concentrations of crosslinkable PEGs.

In a still further presently preferred embodiment, multiple alginate-PLL-alginate microcapsules are entrapped in an (ionically and/or covalently crosslinkable) alginate macrocapsule, followed by a covering of PEG such that PEG and alginate are in intimate contact, and the PEG is exposed on the surface of the macrocapsule. In this embodiment as well, the polycation layer is optional because the PEG outer coat can readily provide immunoprotectivity by selection of appropriate molecular weights and concentrations of crosslinkable PEGs.

In still another presently preferred embodiment, biologically active material is entrapped directly in a macrocapsule comprising ionically and/or covalently crosslinkable alginate, and/or covalently crosslinkable linear or branched chain PEG.

The invention will now be described in greater detail with reference to the following non-limiting examples.

EXAMPLE 1

Preparation Of PEG Diacrylate Using Acryloyl Chloride

PEG of molecular weight 18500 (abbreviated 18.5 k, also available commercially as PEG 20M) was modified chemically using the following procedure to incorporate acrylate functionalities into the molecule which rendered it polymerizable. Other PEGs ranging in molecular weights from as low as 200 to as high as (but not limited to) 35000 could also be modified by the same procedure.

PEG 18.5 k was dried thoroughly by heating in a vacuum oven at 80° C. for 24 hours. Alternately, the PEG could be dissolved in toluene and the solution distilled wherein any moisture could be removed as an azeotrope with toluene. 20 g of dry PEG were dissolved in 200–250 ml of dry toluene (acetone, benzene, and other dry organic solvents may also be used). A twofold molar excess of acryloyl chloride was used (0.35 ml) and a base, triethyl amine (0.6 ml) was added to remove HCl upon formation. Before addition of acryloyl chloride, the solution was cooled in an ice bath. The reaction was carried in a round bottomed flask under argon with constant reflux for 24 hours. The reaction mixture was filtered to remove the insoluble triethyl amine hydrochloride while the filtrate was added to an excess of ether to precipitate PE diacrylate. The product was redissolved and precipitated twice for further purification and any remaining solvent removed in vacuum. Other purification schemes such as dialysis of a PEG-water solution against deionized water followed by freeze drying are also acceptable. Yield: 17 g.

EXAMPLE 2

Alternate Methods for Preparation of Polymerizable PEG

Several other methods may be utilized to prepare a modified PEG that is polymerizable or crosslinkable by introducing unsaturation at the ends of the PEG chain. Some of these methods are briefly outlined below.

An esterification reaction between PEG and acrylic acid (or higher homologue or derivative thereof) may be carried out in an organic solvent such as toluene. A small amount of acid such as p-toluene sulfonic acid may be used to catalyze the reaction. Excess of one of the reactants (acrylic acid) will drive the reaction towards the products. The reaction is refluxed for several hours. Since water is formed as a product of the reaction, in order to drive the equilibrium towards the products, it may be continuously withdrawn by distillation of the azeotrope formed with toluene. Standard purification schemes may be utilized. Methacrylic acid or methacrylate may be reacted in a similar fashion with PEG to obtain the polymerizable derivative (Fukui and Tanaka, 1976).

Alternatively, the method of Mathias et al. (1982) which involves the reaction of the PEG alkoxide with acetylene gas to produce the vinyl ethers of PEG may be employed to produce a polymerizable PEG derivative.

A reaction between PEG and allyl chloride in a dry solvent catalyzed by small amounts of stannic chloride also results in a polymerizable PEG.

Several other techniques may be utilized to obtain polymerizable PEG derivatives. Harris (1985) describes a number of protocols involving PEG chemistry from which alternative synthetic schemes are provided.

EXAMPLE 3

Visible Light Photopolymerization To Produce PEG Gels

PEG derivatives prepared by the techniques outlined in examples 1 and 2 were dissolved in aqueous bicarbonate buffered saline (such as 5–40 wt %, or other buffer) at pH 7.4. The photosensitizer, ethyl eosin (0.01 µM up to 0.1M), a cocatalyst, triethanolamine (0.01 µM up to 0.1M), and comonomer, vinyl pyrrolidinone (0.001 to 10%, but not essential) were added to the solution which was protected from light until the photopolymerization reaction. In the alternative, other initiators cocatalysts, comonomers and wavelengths of laser radiation may be used, the selection of which is well known in the art.

A small quantity of the prepared solution was taken in a test tube and exposed to visible radiation either from an argon ion laser at a wavelength of 514 nm at powers between 10 mW to 2 W, or a 100 watt mercury arc lamp which has a fairly strong emission around 514 nm. The gelling time was noted and found to be extremely rapid with the laser (on the order of milliseconds) and fairly rapid with the mercury lamp (on the order of seconds) and varied with the concentrations of polymer, initiator, cocatalyst, and comonomers in the system.

EXAMPLE 4

UV Light Photopolymerization To Produce PEG Gels

A different initiating system from the one above was used to produce PEG gels. A UV photoinitiator, 2,2-dimethoxy-2-phenyl acetophenone was added to a solution of polymerizable PEG in aqueous buffer at a concentration of 1000–1500 ppm. This solution was exposed to long wave UV radiation from a 100 watt UV lamp. The time required for gellation was of the order of seconds and was a function of the concentrations of initiator and addition of other polymerizable monomers such as vinyl pyrrolidone (0.001 to 10%). A UV laser may also be used for the photopolymerization. Other UV photoinitiators may also be used (e.g., benzoin ethyl ether).

EXAMPLE 5

Geometries of Microcapsule-Containing PEG Gels for Implantation

Microcapsules of alginate or any other material containing cells or enzymes or drugs may be delivered and retrieved from an implant using varying geometries of the microcapsule-containing PEG gels. A large number of individual microcapsules may be localized to a preferred region in the peritoneal cavity (or other implantation site) by embedding these microcapsules in a crosslinked PEG gel. Various geometries may be considered for implantation such as cylindrical rod, circular disk, flat plate, dog bone, and long cylindrical "laces" or "threads" or "worms."

Regardless of the geometry, the formation of the final implantable products required similar processing techniques. The cell containing microcapsules were suspended in a physiological solution of PEG 18.5K diacrylate (30 wt %; PEGs of varying molecular weights may be used) containing triethanolamine (0.01 µM up to 0.1M), ethyl eosin (0.01 µM up to 0.1M), and vinyl pyrrolidinone (0.001 to 10%). This suspension was exposed to visible light from a laser or mercury lamp which caused rapid crosslinking of PEG-diacrylate and resulted in microcapsules embedded in the PEG gel.

In order to produce a cylindrical "lace," a suspension is disposed in a hypodermic needle having a suitable gauge needle or cannula and the emergent stream is expelled into a buffered solution (which may have multivalent cations if alginate is used in the suspension) and simultaneously exposed to laser radiation from a suitable lamp source if photopolymerization is required for the reaction. The lamp could be a laser light source or a UV light source depending upon the material to be polymerized and the photoinitiator used, as is known in the art. Crosslinking is instantaneous, i.e., the emerging stream is photocrosslinked as fast as it is extruded, resulting in the formation of a "lace" or "noodle." Gels or other geometries can be produced from appropriate molds fabricated for the purpose.

EXAMPLE 6

Alginate Gel Entrapment Of Microencapsulated Islets

Canine islets were isolated from donor pancreata by collagenase digestion and purified using a physiological islet purification solution. Islets were then encapsulated in an alginate-polylysine alginate microcapsule by the following process: Ten thousand purified islets were suspended in 1.8% solution of Na alginate (G content 64%) and via an air-droplet generating device, islets were entrapped in alginate gel beads by crosslinking alginate in 0.8% $CaCl_2$ solution. A polylysine membrane was formed following suspension of these alginate encapsulated islets in a 0.1% polylysine solution for 4–8 minutes. The encapsulated islet was then coated with an outer layer of alginate by suspension in 0.2% alginate for 5 minutes.

A cylindrical tube (i.e., a lace, approximately 1–5 mm in diameter) of alginate encasing these microencapsulated islets was then produced as follows:

The microencapsulated islets were suspended in 1.8% alginate in the ratio of 1 volume microcapsule pellet to 4 volumes of alginate, and extruded into a solution of divalent cations containing $CaCl_2$ alone, or a combination of barium and calcium chloride. The ratio of barium and calcium chloride as a combination of divalent cations crosslinking agent could vary from 1:10 to 1:100 (barium:calcium), and the preferred ratio is in the range of 1:50 to 1:100. By combining barium and calcium, a gel of greater strength results. Thus, by this process of ionic crosslinking, approximately 8000 microencapsulated islets are entrapped in a 16 cm long cylindrical tube of alginate gel.

Alternatively, spherical macrocapsules containing microencapsulated islets can be prepared by introducing droplets of the above-described solution (i.e., microencapsulated islets in alginate solution) into a bath containing polyvalent cations (e.g., $Ca^{++}$), as described above.

EXAMPLE 7

Variations in Composition of Retrievable Systems

A number of variations in compositions and materials used in the design of retrievable systems are acceptable and advantageous. The crosslinked alginate or PEG spheres (or lace) containing alginate microcapsules may be replaced in the appropriate situations by an ionically and/or covalently crosslinked alginate spheres. Combinations of alginate and PEG may also be used. The following variations, among others, are possible:

(i) PEG alone, crosslinked as described above; mixtures of different molecular weight crosslinkable PEGs (linear or branched chain) may be used to adjust permeability of the resultant gels;

(ii) Alginate alone, ionically crosslinked;

(iii) Alginate alone, modified to be both ionically and covalently crosslinkable;

(iv) A combination of ionically crosslinkable alginate and covalently crosslinkable PEG (linear or branched chain);

(v) A combination of modified alginate (i.e., ionically and covalently crosslinkable) and covalently crosslinkable PEG (linear or branched chain);; and (vi) An ionically and/or covalently crosslinked alginate macrocapsule (e.g., a sphere or lace) covered with a coating of covalently crosslinked PEG (linear or branched chain) covering the exterior such that the PEG and alginate are in intimate contact.

Ionic crosslinking of alginate can be accomplished with either $Ca^{++}$ alone or a combination of $Ba^{++}$ and $Ca^{++}$ in a ratio of 1:10 to 1:100 (Ba:Ca).

The alginate referred to in the preceding paragraph may be replaced with a modified alginate that is chemically crosslinkable in addition to its ionic gelling capabilities. The modified alginates mentioned herein are described in detail in copending patent application Ser. No. 07/784,267, incorporated by reference herein in its entirety.

The PLL referred to above may also be replaced with a modified PLL that is covalently crosslinkable. The modified PLL mentioned herein is described in detail in copending patent application Ser. No. 07/784,267, incorporated by reference herein in its entirety.

EXAMPLE 8

Kinetics of Insulin Diffusion from Gel Entrapped Microencapsulated Islets: In Vitro Studies Kinetics of insulin secretion from the gel entrapped encapsulated canine islets were compared to individual microencapsulated islets or unencapsulated canine islets as follows: either free unencapsulated canine islets (controls) or encapsulated canine islets or gel entrapped encapsulated canine islets were incubated in RPMI culture medium containing a basal level of 60 mg % glucose for 60 minutes, then transferred to medium containing a stimulatory level of 450 mg % glucose for 60 minutes and returned to basal medium (60 mg % glucose) for a further 60 minutes. These tests were performed in triplicate. The supernatant was collected at the end of each 60 minute period. Insulin secretion was assayed by measuring insulin concentration (µU/ml per islet equivalent count) in the supernatant, using RIA.

The study was repeated, but in addition, 10 mM theophylline was added to the 450 mg % glucose as an added stimulus of insulin secretion. The results of these studies are shown in Table 1.

TABLE 1

In Vitro Insulin Secretion in Response to Static Glucose Stimulation

| | INSULIN (µU/ml/islet/hr) | | | | | |
|---|---|---|---|---|---|---|
| | ACTUAL VALUE | | | INSULIN RATIO ABOVE BASAL | | |
| | Basal | Stimulated | Basal | Basal | Stimulated | Basal |
| I. Unencapsulated Islets | | | | | | |
| A. Glucose Stimulated | | | | | | |
| Mean | 3.50 | 5.40 | 6.10 | 1 | 1.45 | 1.50 |
| Standard Deviation | 2.55 | 4.81 | 6.22 | 0 | 0.35 | 0.71 |
| B. Glucose + Theophylline | | | | | | |

TABLE 1-continued

In Vitro Insulin Secretion in Response to Static Glucose Stimulation

| | INSULIN (μU/ml/islet/hr) | | | | | |
|---|---|---|---|---|---|---|
| | ACTUAL VALUE | | | INSULIN RATIO ABOVE BASAL | | |
| | Basal | Stimulated | Basal | Basal | Stimulated | Basal |
| Mean | 5.40 | 15.45 | 11.20 | 1 | 3.00 | 2.15 |
| Standard Deviation | 1.56 | 0.50 | 2.26 | 0 | 0.71 | 0.21 |
| II. Microencapsulated Islets | | | | | | |
| A. Glucose Stimulated | | | | | | |
| Mean | 4.77 | 7.03 | 5.08 | 1 | 1.50 | 1.15 |
| Standard Deviation | 3.30 | 5.77 | 2.80 | 0 | 0.66 | 0.30 |
| B. Glucose + Theophylline | | | | | | |
| Mean | 4.01 | 21.63 | 6.45 | 1 | 5.02 | 1.35 |
| Standard Deviation | 2.62 | 26.36 | 4.26 | 0 | 2.86 | 0.32 |
| III. Entrapped Microencapsulated Islets | | | | | | |
| A. Glucose Stimulated | | | | | | |
| Mean | 6.85 | 17.30 | 13.43 | 1 | 2.40 | 2.00 |
| Standard Deviation | 4.61 | 14.43 | 9.02 | 0 | 0.80 | 0.18 |
| B. Glucose + Theophylline | | | | | | |
| Mean | 5.10 | 38.30 | 31.68 | 1 | 8.28 | 6.45 |
| Standard Deviation | 3.41 | 26.40 | 18.43 | 0 | 6.50 | 2.22 |

One skilled in the art would expect that entrapping encapsulated canine islets in a further outer coat of polymer material would result in decreased response to a stimulus and reduced diffusion of insulin. That is, entrapping encapsulated islets in yet a second layer of polymer material [the microcapsule plus the macrocapsule] would be expected to reduce the responsiveness of the encapsulated islet to an outside stimulus. Unexpectedly, according to the present invention, it has been found that the rapidity and intensity of the in vitro response of gel entrapped, microencapsulated islets was equal to, if not better than, the free floating encapsulated islets (as shown in Table 1).

Following stimulation with 450 mg % glucose alone, the insulin response (see Table 1) from the microencapsulated islets immobilized in a macrogel ("entrapped MC") was equal to, if not better than the free floating microencapsulated islets ("Free MC") as well as the free unencapsulated islet controls ("Free Islets"). This phenomenon was also observed in response to 450 mg % glucose+ 10 mg theophylline stimulus. While not wishing to be bound to any particular theory, it is currently hypothesized that this surprising result is explained by the fact that insulin is a negatively charged protein, and with the release of insulin from the entrapped microencapsulated cells in response to glucose stimulus, the negatively charged insulin is electrostatically discharged from the negatively charged entrapping gel material, thus accelerating the response time of insulin release. Enhancement of insulin release from microencapsulated islets within a macrogel, as compared to insulin release from individual encapsulated islets, can also be explained by the fact that the microcapsule is more neutrally charged than the macrocapsule, due to the presence of the positively charged PLL in the microcapsule membrane. This unexpected result was corroborated in the in vivo studies (described in Example 9) where the fall in serum glucose in response to an intravenous glucose injection occurred rapidly in diabetic rats treated with gel entrapped microencapsulated canine islets (see FIG. 3), suggestive that gel entrapment provides an added advantage of improved insulin response to a systemic glucose signal.

The results shown in Table 1 demonstrate that gel entrapment of encapsulated canine islets did not impair insulin secretion in response to a glucose stimulus or in response to glucose plus theophylline. Return of insulin levels to basal state was however delayed in the macrocapsule experiment, and is consistent with entrapment of insulin in the outer gel, resulting in effect a sustained release drug delivery system. In in vivo applications, this sustained release of insulin may provide a more stable homeostatic mechanism.

Thus gel entrapment of microencapsulated islets provides several unexpected advantages with regard to insulin secretion:

(i) rapid response of insulin release to a glucose stimulus, and (ii) once the insulin is released, a slow return to basal state, providing a sustained, continuous release over a longer period.

Both of these responses are important in improving the homeostatic control of glucose metabolism in the diabetic recipient.

EXAMPLE 9

In Vivo Studies of Gel Entrapped Microencapsulated Islets

The efficacy of gel-entrapped microencapsulated canine islets was compared to free-floating encapsulated canine islets in the treatment of streptozoticin-induced (STZ) diabetic Lewis rats. Eight thousand encapsulated canine islets (either free-floating, or entrapped in cylindrical tubes of alginate) were implanted into the peritoneal cavities of four STZ-diabetic Lewis rats, and compared with eight thousand unencapsulated canine islets (controls) implanted in the same way.

To ensure no variability in the viability, purity and function of the islet preparation, islets from the same canine pancreatic donor were used in both free floating microencapsulated and gel entrapped microencapsulated groups. Furthermore to ensure no variability in the integrity and formation of the microcapsules themselves, the islets were all encapsulated in one batch process and then divided into two—one half being used for free floating implantation and the remaining half entrapped in an alginate macrocapsule (i.e., gel entrapped microencapsulated islets) prior to implantation.

Figure 2:
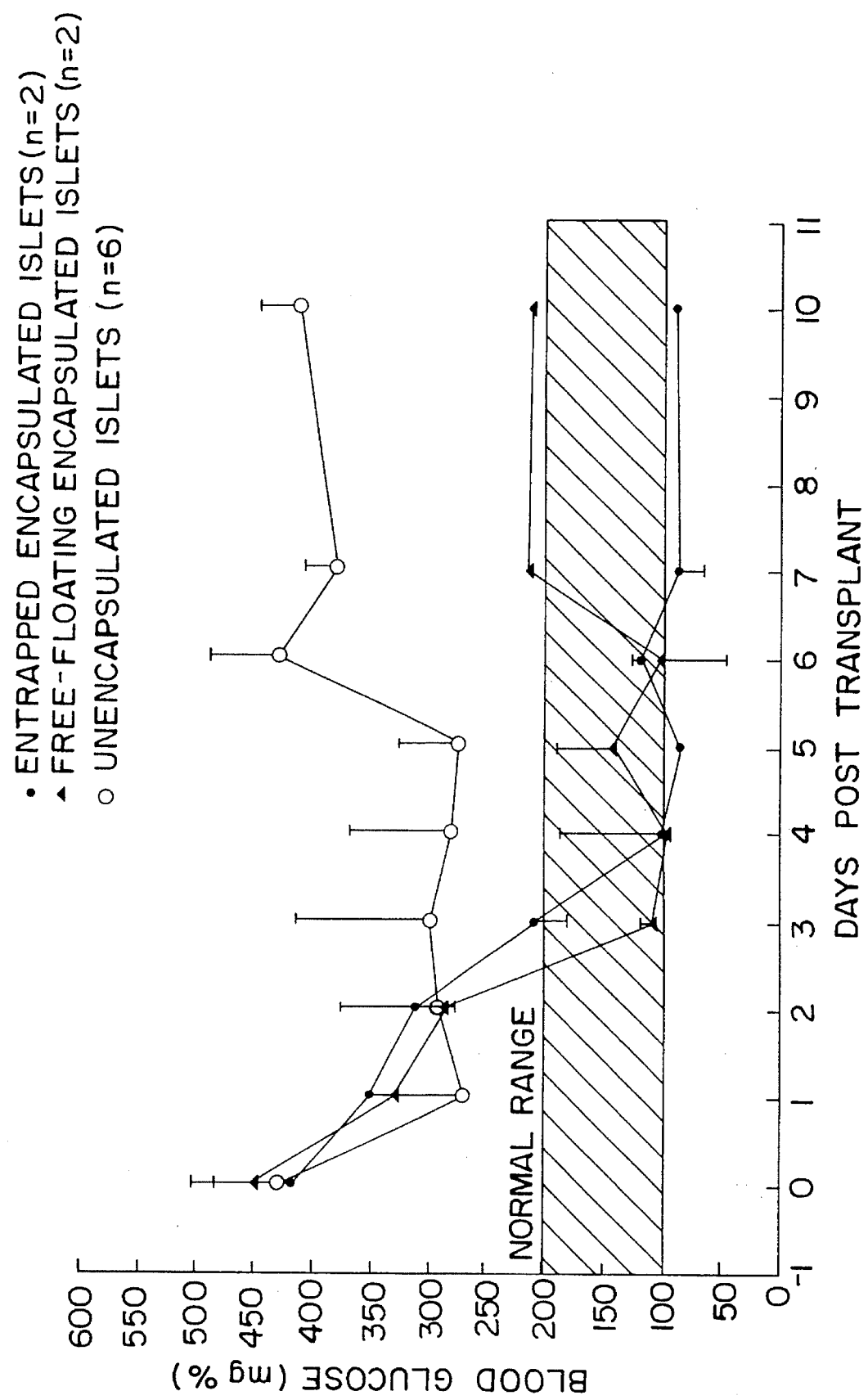
FIG. 2 is a graph of the blood glucose of rats implanted with entrapped encapsulated islets according to the present invention (filled circle ●), free-floating encapsulated islets (filled triangle) and unencapsulated islets (open circle ○) over time, when the islets are xenografts (canine islets).

Immunoprotectivity, biocompatibility, function and graft survival of the unencapsulated (free) islets compared to free-floating encapsulated islets (in microcapsules only) compared to entrapped encapsulated islets (in macrocapsules with microcapsules therein) were compared by measuring:

(i) Daily serum glucose levels (see FIG. 2)

Diabetes is induced in rats by STZ injection. Injected rats are considered diabetic if serum glucose levels are greater than 200 mg %. Unencapsulated canine islets (free islets) failed to restore normoglycemia (serum glucose levels less than 200 mg %) in the diabetic rat. In contrast, the free floating microencapsulated islets and the macroencapsulated islets both restored normoglycemia in these diabetic rats by the 3rd–4th day. By day 7, the free floating microencapsulated islets began to fail, with serum glucose levels rising in these recipients to >200 mg %. In contrast, rats receiving gel entrapped microcapsules (macrocapsules) continued their normoglycemic state, with serum glucose levels below 100 mg % (FIG. 2). These in vivo studies therefore provide evidence that (compared to free floating microencapsulated islets) gel entrapment of microencapsulated islets prolongs graft survival, presumably by enhancing cytoprotectivity and biocompatibility.

(ii) daily urine volume

With onset of diabetes, urine volume increases. Following STZ injection, urine volume exceeds 30 ccs per day and is indicative of the diabetic state. With resolution of diabetes, urine volume falls to normal levels. Reduction in urine volume coincided with the fall in serum glucose, providing further evidence that graft function and survival of macroencapsulated islets was superior to both free unencapsulated islets and free floating microencapsulated islets. On day 7, urine volume in free floating microencapsulated group rose to diabetic levels (>30 mls.), indicating onset of graft failure, while the rats receiving gel entrapped microcapsules (i.e., macrocapsules) maintained a normal level of urine output, indicating ongoing graft function.

(iii) body weight

Following STZ injections, diabetic rats lose weight dramatically. Maintenance of weight or weight gain is an excellent parameter of function of the transplanted islets. Similar to the correlation between urine volume and serum glucose levels, changes in body weight corroborated the above analysis, providing further evidence that rats receiving macroencapsulated islets retained normal graft function compared to graft failure in rats receiving free unencapsulated islets and those receiving free floating microencapsulated islets. Body weight improved significantly in the animals receiving gel entrapped microcapsules (i.e., macrocapsules), while weight loss as a result of diabetes continued in the animals with free unencapsulated islets and fell after day 7 in the animals with free floating encapsulated islets.

Figure 3:
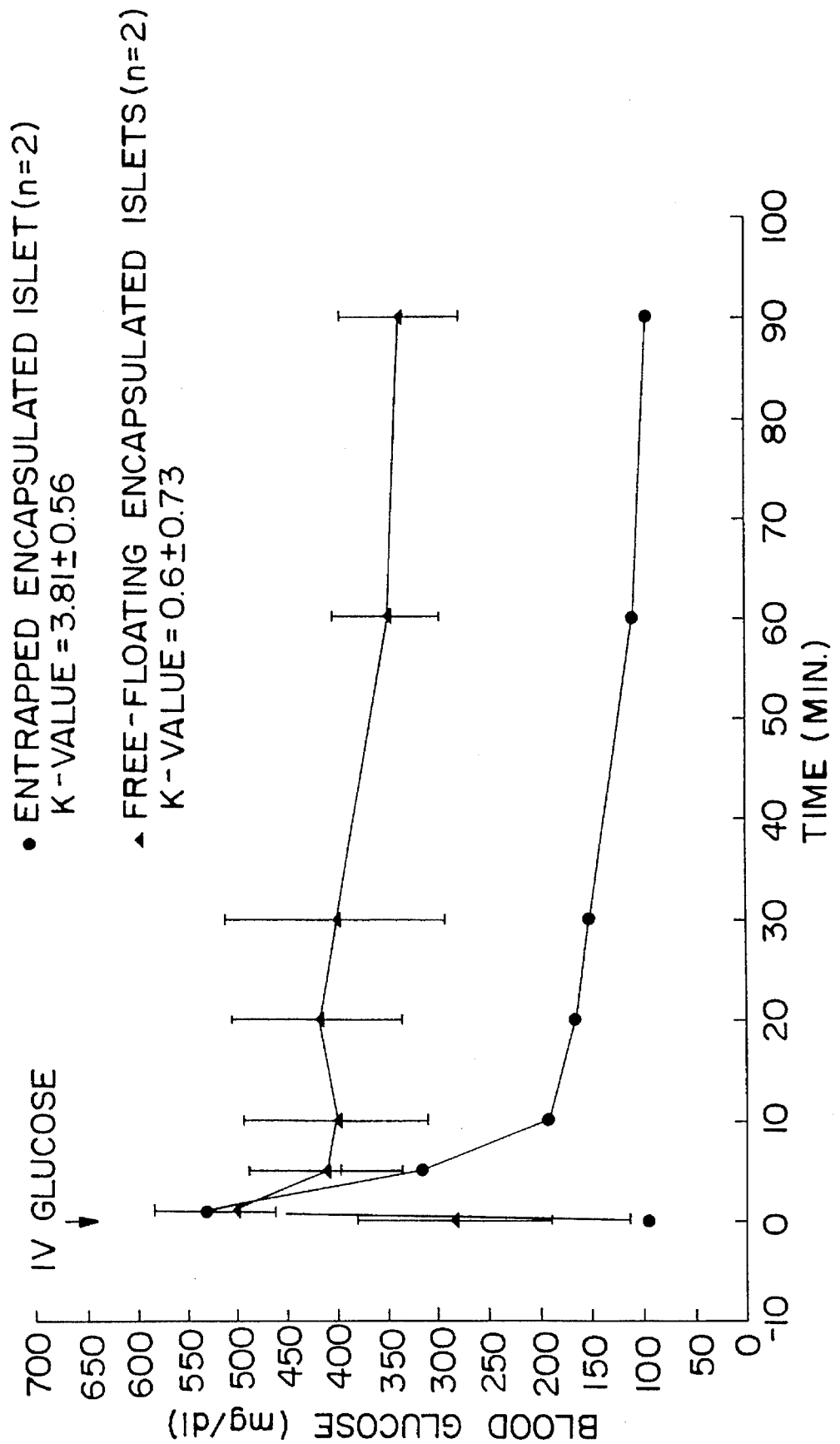
FIG. 3 is a graph of the serum glucose response to an intravenous glucose challenge (IVGTT) in rats treated with macroencapsulated canine islets according to the present invention, compared to the response in rats transplanted with free floating microencapsulated canine islets 7 days after implantation of the microcapsules and macrocapsules.

(iv) glucose response to systemic glucose challenge (intravenous glucose tolerance test, IVGTT; see FIG. 3)

An IVGTT provides an in vivo assessment of the kinetics of insulin release in response to an intravenous glucose challenge. By calculating the rate of fall of glucose over time, a numerical value (K-value) can be ascertained and compared to normal non-diabetic rats. The more rapid the fall in serum glucose following the glucose challenge, the higher the K-value. The fall in serum glucose in response to an intravenous glucose challenge was studied in both the rats receiving macroencapsulated and free floating microencapsulated islets. Serum glucose was measured at 1, 4, 10, 20, 30, 60 & 90 minutes following an intravenous injection of 0.5 cc per kg of 50% dextrose. As can be seen in FIG. 3, following the intravenous glucose injection, serum glucose rose to 489 mg % in the macroencapsulated group, and then fell rapidly to normal levels within 10 minutes, indicating an excellent in vivo insulin response to the systemic glucose challenge. K-value (which represents the % fall of glucose over time) in these animals was normal ($3.81\pm0.56$). This unexpected rapid insulin response corroborates the in vitro findings described in Example 8, i.e., that alginate gel entrapped microcapsules respond rapidly to a glucose stimulus, and provides further evidence that a potential advantage of alginate gel entrapment is electrostatic repulsion of negatively charged insulin from within the capsule, and hence rapid physiological fall in glucose in response to a systemic challenge.

The K values of the rats receiving macrocapsules were significantly better ($K=3.8\pm0.56$) than the rats receiving free floating encapsulated islets ($K=0.6\pm0.73$), indicating loss of graft function in the rats receiving free-floating encapsulated islets. Since the islets transplanted into both groups were from the same canine donor, and the volume of islets employed were identical, this difference in response reflects the improved immunoprotectivity of the macrocapsule.

Figure 4:
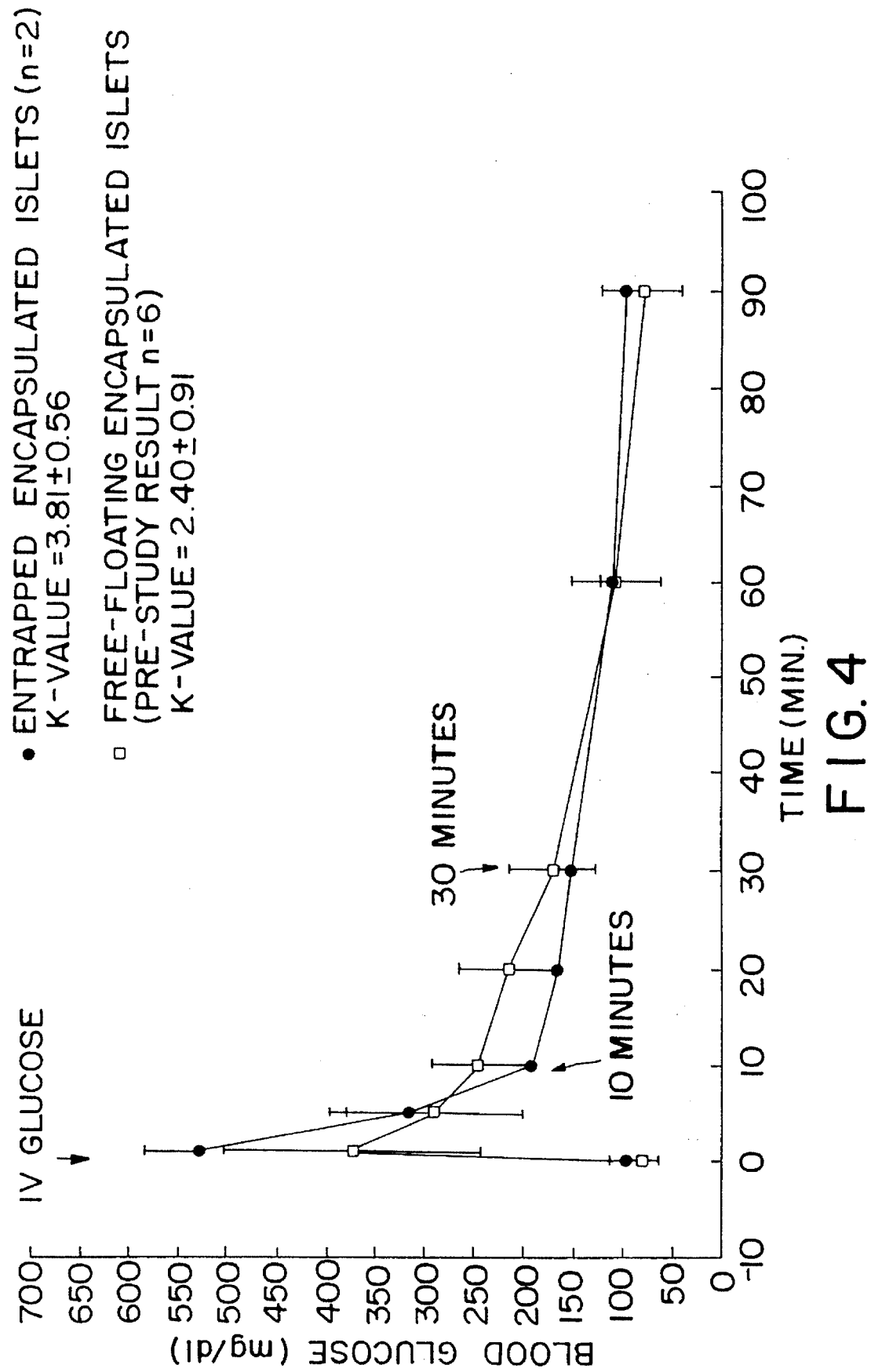
FIG. 4 is a graph of the serum glucose response to an intravenous glucose challenge (IVGTT) in rats treated with macroencapsulated canine islets according to the present invention, compared to the response in rats transplanted with free floating microencapsulated canine islets.

In a separate experiment, free floating encapsulated canine islets were transplanted into diabetic rats and IVGTT performed in these recipients while graft function was normal (serum glucose less than 100 mg %). As can be seen in FIG. 4, the serum glucose fell to normal levels following the intravenous injection of dextrose only after 30 minutes (K value $2.4\pm0.9$) compared to the more rapid fall of glucose (within 10 minutes) in the rats receiving macroencapsulated islets (K value $3.81\pm0.56$).

From the above-described in vivo studies, it can be concluded that:

(i) gel entrapment of microencapsulated islets does not decrease the rate of diffusion of insulin in response to a glucose stimulus both in vitro and in vivo;

(ii) gel entrapment of microencapsulated islets in fact enhances insulin release; and (iii) gel entrapment of microencapsulated islets prolongs graft function.

EXAMPLE 10

Retrieval of Gel Entrapped Microencapsulated Islets

Gel entrapped microencapsulated islets were implanted into STZ induced diabetic rats and followed for 14 days. Normal serum glucose levels were achieved within 3 days, and was maintained for the entire observation period. On the 14th day, the macrogelled encapsulated islets were retrieved and examined microscopically.

As observed by photomicrograph, viable intact islets within entrapped microcapsules were found with no evidence of cellular overgrowth of the outer surface layer of the macrogel. A photomicrograph (100x) of a macrocapsule containing canine islets according to the present invention retrieved from the peritoneal cavity of an STZ-diabetic Lewis rat 14 days after implantation demonstrates a smooth surface on the outer exposed layer of the macrocapsule, with no evidence of cellular overgrowth. Encapsulated viable individual canine islets can be seen contained within the macrocapsule. At the time of retrieval, this diabetic rat was normoglycemic.

Figure 5:
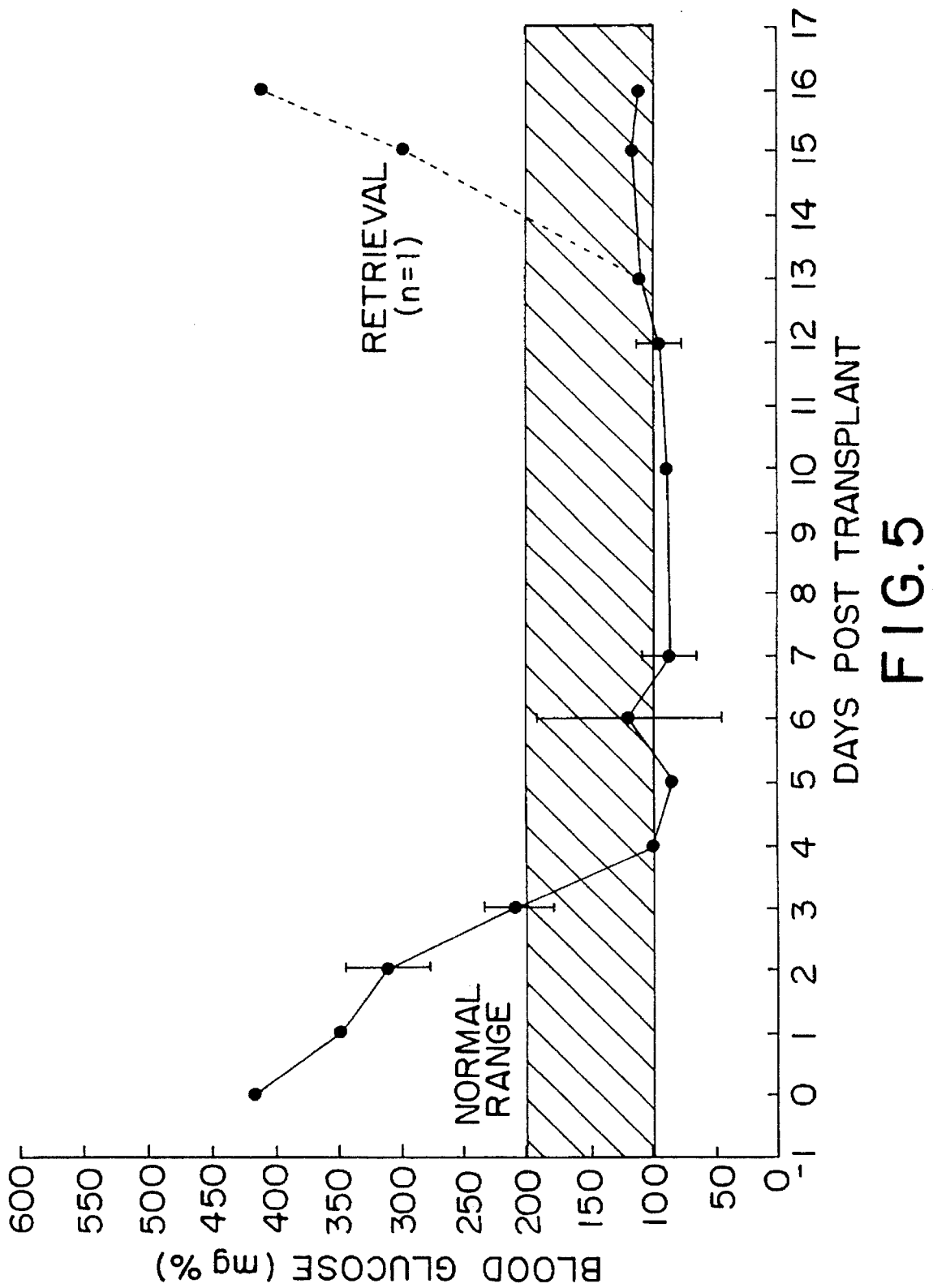
FIG. 5 is a graph of blood glucose levels of rats implanted with entrapped encapsulated islets according to the present invention (filled circle ●) over time, when the islets are xenografts (canine islets). On day 14, the entrapped encapsulated islets were retrieved. The diabetic state recurred within 24 hours following retrieval of the entrapped encapsulated islets, proving the viability of the islets entrapped within the macrocapsule of the present invention.

Serum glucose levels were monitored in the rat following retrieval of the macrogelled encapsulated islets. As can be seen in FIG. 5, within 24 hours after retrieval of the macrocapsule serum glucose levels rose to greater than 200 mg %, indicating that the macrogelled encapsulated islets was responsible for normalization of the serum glucose, and providing further evidence of the immunoprotectivity and biocompatibility of the macrocapsule.

From these studies, it can be concluded that:

(i) gel entrapment provides a smoother outer surface, a reduced exposed surface area and hence increased biocompatibility than free floating microencapsulated islets.

(ii) gel entrapment increases the mechanical stability of encapsulated islets and provides a retaining matrix even if the individual capsules were to break.

EXAMPLE 11

Alleviation of Diabetic Symptoms in a Spontaneous Diabetic Dog Implanted with Invention Macrocapsules A spontaneous diabetic dog having the classical symptoms of Type I Diabetes mellitus at the time of diagnosis, i.e., clinical signs such as polyuria, polydipsia, polyphagia, weight loss, persistent fasting hyperglycemia (i.e., blood glucose >250 mg/dl), persistent glycosuria, and the need for 1–2 daily injections of insulin to prevent rapid decompensation, was chosen as a recipient for transplantation of a macrocapsule of the invention (containing a plurality of microencapsulated islets).

Islets from a healthy canine donor were isolated employing conventional methods (e.g., collagenase digestion). Islets were then microencapsulated as described above (see, for example, Example 6), in conventional alginate-PLL-alginate microcapsules (approximately 600 microns in diameter). The microcapsules were then further entrapped (i.e., encapsulated) into macrocapsules (spherical beads about 4000–8000 microns) of ionically crosslinked alginate by extrusion of a suspension of microcapsules in an alginate solution into a bath containing calcium chloride. Approximately 60–80 microcapsules were entrapped within a single macrocapsule.

Prior to transplantation, the dog had been maintained on a regimen of 12 Units of insulin per day. The transplantation was performed under general anaesthesia through a 1.5 ventral midline incision, and the macrocapsules aseptically introduced into the peritoneal cavity through a stainless steel funnel. The dog received a transplant dose of about 20,000 islets/kg body weight. The incision was then closed by sutures. A regimen of prednisolone was maintained for 14 days post-transplant as an anti-inflammatory. Fasting blood glucose, plasma C-peptide, urine output and body weight were measured daily for the first 14 days post-transplant, and every 7 days thereafter. Intravenous glucose tolerance tests (IVGTT) were performed 7 days prior to transplantation, 14 and 30 days post-transplantation, and every 30 days thereafter.

All measured parameters returned to normal non-diabetic values within three days after transplantation. Blood glucose was maintained well below 200 mg/dl, and the dog remained euglycemic for >150 days following transplantation, without the need for any exogenous insulin. IVGTT results were normal and showed rapid glucose clearance following challenge with a bolus of glucose.

EXAMPLE 12

Reversal of Hepatic Deficiency by Transplantation of Encapsulated Hepatocytes in a Gunn Rat Model Homozygous Gunn rats having a deficiency of the liver enzyme uridine diphosphate glucuronyl transferase (UDPGT) and resultant elevated serum bilirubin levels (a condition commonly known as jaundice) were chosen as a model of hepatic deficiency. Heterozygous Gunn rats which carry the abnormal gene, but are free from jaundice were chosen as the donors of hepatocytes for cellular transplant.

The donor liver was cannulated via the portal vein with silicone tubing (i.d. 0.025 inch, o.d. 0.047 inch) and perfused with 100 ml of 0.05% collagenase (Sigma, Type IV) in 15 minutes. The hepatocytes were then harvested into a sterile beaker and washed three times with RPMI medium. Viability of the isolated hepatocytes was tested by acridine orange/propidium iodide staining and found to be greater than 80%.

The hepatocytes were encapsulated into conventional alginate-PLL-alginate microcapsules as described above. These microcapsules were further entrapped (or encapsulated) in spherical macrocapsules of ionically crosslinked alginate (as described above. Approximately 50–100 microcapsules were entrapped in a single macrocapsule. Each recipient received ~$10^7$ encapsulated hepatocytes. The macrocapsules were implanted in the peritoneal cavity of the recipients.

Prior to transplantation, recipient billrubin levels were 5.3±0.3 mg %. By the second week post-transplantation, serum bilirubin levels were reduced to 2.05±1.05 mg %, which was significantly lower than pre-transplant levels. These reduced levels were maintained for an average of 73±4 days. All recipients received cyclosporin A as an anti-inflammatory (10 mg/kg, i.e., at levels lower than required to prevent immune rejection. Thus, the feasibility and efficacy of the macrocapsule of the invention is demonstrated for in vivo transplantation of hepatocytes.

While the invention has been described in detail with reference to certain preferred embodiments thereof, it will be understood that modifications and variations are within the spirit and scope of that which is described and claimed.

REFERENCES

Abuchowski et al., 1977; J. Biol. Chem. 252:3578.

Collins et al., U.S. Pat. No. 4,938,961.

Decker and Moussa, 1989; Macromolecules 22:4455.

Desai and Hubbell, 1991a; Biomaterials 12:144–153.

Desai and Hubbell, 1992a; Biomaterials 13:505–510.

Desai and Hubbell, 1992b; Biomaterials 13:417–420.

Soon-Shiong et al., 1991; U.S. Ser. No. 07/784,267.

Dupuy et al., 1988; J. Biomed. Mater. Res. 22:1061.
Duval et al., 1991; Carbohydrate Polymers 15:233.
Eaton, D. F., 1986; Advances in Photochemistry 13:427.
Fukui and Tanaka, 1976; FEBS Letters 66:179.
Fukui et al., 1987; Methods in Enzymology 135:230.
Harris, J. M., 1985; JMS-Rev. Macromol. Chem. Phys. C25:325.
Harris et al., 1984; J. Polym. Sci., Polym. Chem. Ed. 22:341.
Hoyle et al., 1989; Macromolecules 22:3866.
Karu, T. I., 1990, Photochemistry and Photobiology 1089.
Kumakura and Kaetsu, 1983; J. Appl. Polym. Sci. 28:2167.
Lim and Sun, 1980; Science 210:908.
Mathias et al., 1982; J. Polym. Sci., Polym. Lett. Ed. 20:473.
Nagoaka and Nakao, 1990; Biomaterials 11:119.
Otterlei et al., 1991; J. Immunotherapy 10:286–291.
Pitha et al., 1979; Eur. J. Biochem. 94:11.
Soon-Shiong et al., 1991; Trans. 3rd Intl. Cong. on Pancreatic & islet transplantation, June 6–8, Lyon, France, p.6.
Soon-Shiong et al., 1991; Transplantation Proc. 23:758.
Weiner et al., 1974, Israel J. Chem. 12:863.
Wu, D. S., November 1990; Laser Focus World, p 99.
Zalipsky et al., 1983, Eur. Polym. J. 19:1177.
Zheng et al., 1991; Transplantation 51:63.

We claim:

1. A macrocapsule for encapsulating biologically active materials, said macrocapsule comprising a first biocompatible gel selected from the group consisting of:
   covalently crosslinkable alginate;
   ionically crosslinkable alginate;
   covalently and ionically crosslinkable alginate;
   covalently crosslinkable linear PEG;
   covalently crosslinkable branched chain PEG;
   mixtures of different molecular weight covalently crosslinkable linear or branched chain PEG;
   combinations of alginate and PEG; and
   mixtures of any two or more thereof,
   wherein said macrocapsule further comprises:
   a plurality of microcapsules,
   i) wherein said microcapsules contain said biologically active materials therein;
   ii) wherein said microcapsules are formed of a second biocompatible gel selected from the group consisting of:
   covalently crosslinkable alginate;
   ionically crosslinkable alginate;
   covalently and ionically crosslinkable alginate;
   covalently crosslinkable linear PEG;
   covalently crosslinkable branched chain PEG;
   mixtures of different molecular weight covalently crosslinkable linear or branched chain PEG;
   combinations of alginate and PEG; and
   mixtures of any two or more thereof;
   iii) wherein said microcapsules are each individually treated with an immunoprotective coating, wherein said immunoprotective coating is a polycation; and
   iv) wherein said second biocompatible gel may be the same or different from said first biocompatible gel.

2. A macrocapsule according to claim 1 wherein said polycation is polylysine.

3. A macrocapsule according to claim 1 wherein said macrocapsule is formed in the shape of a cylinder, sphere, disc, flat sheet, wafer or dog-bone.

4. A delivery system for pharmacologically active agents comprising a macrocapsule according to claim 1, wherein said biologically active material is a pharmacologically active agent.

5. A delivery system for pharmacologically active agents comprising a macrocapsule according to claim 1, wherein said biologically active material is a living cell.

6. A macrocapsule according to claim 1 wherein said first biocompatible gel is high guluronic acid content alginate.

7. A macrocapsule according to claim 1 wherein said second biocompatible gel is an alginate, said immunoprotective coating is polylysine, and said microcapsules further comprise an alginate outer coat on the outside of said immunoprotective coating.

8. A macrocapsule according to claim 1 wherein said first and second biocompatible gels are linear or branched chain polyethylene glycol having a molecular weight ranging from 200 to 1,000,000.

9. A macrocapsule according to claim 1 wherein said first biocompatible gel comprises covalently crosslinkable linear or branched chain polyethylene glycol.

10. A macrocapsule according to claim 1 wherein said first biocompatible gel comprises a combination of ionically and/or crosslinkable alginate and/or covalently crosslinkable linear or branched chain polyethylene glycol.

* * * * *